(12) United States Patent
Ting et al.

(10) Patent No.: US 6,228,790 B1
(45) Date of Patent: May 8, 2001

(54) DINUCLEAR METALLOCENE CATALYST FOR PREPARING HIGH MOLECULAR WEIGHT OLEFIN POLYMER

(75) Inventors: Ching Ting, Hsinchu; Sung-Song Hua, Taipei Hsien; Jing-Cherng Tsai, Kaohsiung; Bor-Ping Wang, Taoyuan, all of (TW)

(73) Assignees: Industrial Technology Research Institute, Hsinchu; Chinese Petroleum Corp.; Taiwan Synthetic Rubber Corporation, both of Taipei, all of (TW)

( * ) Notice: Subject to any disclaimer, the term of this patent is extended or adjusted under 35 U.S.C. 154(b) by 0 days.

(21) Appl. No.: 09/107,074

(22) Filed: Jun. 29, 1998

(51) Int. Cl.$^7$ ..................................................... B01J 31/00
(52) U.S. Cl. .......................... 502/102; 252/103; 252/152; 252/153; 252/155; 252/156; 252/158
(58) Field of Search .................................... 502/102, 103, 502/152, 153, 155, 156, 158

(56) References Cited

U.S. PATENT DOCUMENTS

| | | | |
|---|---|---|---|
| 5,770,318 | * 6/1998 | Friedman | 428/500 |
| 5,770,666 | * 6/1998 | Hamura et al. | 526/134 |
| 5,821,044 | * 10/1998 | Bergathaller et al. | 430/573 |
| 6,010,974 | * 1/2000 | Kim et al. | 502/152 |

* cited by examiner

Primary Examiner—Yogendra Gupta
Assistant Examiner—Derrick G. Hamlin
(74) Attorney, Agent, or Firm—W. Wayne Liauh (57) ABSTRACT

A novel dinuclear metallocene complex is disclosed, which is represented by the following formula (I):

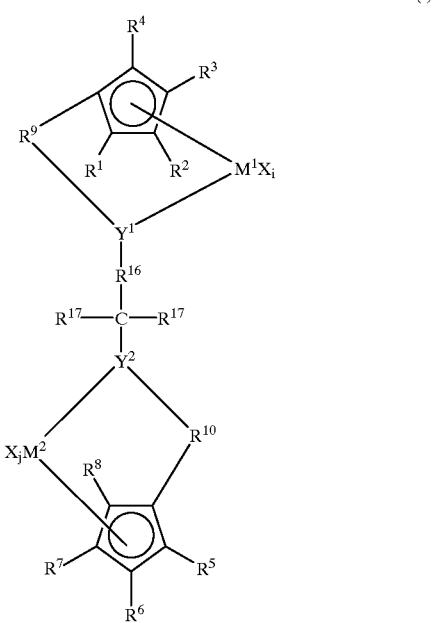

wherein $M^1$ and $M^2$ are the same or different and are independently selected from the group consisting of Group IIIB, Group IVB and Group VB transition metals; each X is the same or different and is indepedently an anionic ligand with −1 valence, which is selected from the group consisting H, $C_{1-20}$ hydrocarbyl, halogen, $C_{1-20}$ alkoxy, $C_{1-20}$ aryloxy, $NH_2$, $NHR^{11}$, $NR^{11}R^{12}$, —(C=O)$NH_2$, —(C=O)$NHR^{13}$, and —(C=O)$NR^{13}R^{14}$, wherein $R^{11}$, $R^{12}$, $R^{13}$ and $R^{14}$ are $C_{1-20}$ alkyl; i is an integer from 1 to 3; j is an integer from 1 to 3, $R^1$, $R^2$, $R^3$, $R^4$, $R^5$, $R^6$, $R^7$, and $R^8$ are the same or different and are independently H, a $C_{1-20}$ linear, branched or cyclic hydrocarbyl group, or a $C_{2-4}$ cyclic hydrocarbylene group which forms a $C_{4-6}$ fused ring system; $Y^1$ and $Y^2$ are the same or different and each is an electron-donating group independently selected from a Group 15 or Group 16 element; $R^9$ and $R^{10}$ are the same or different and each is a divalent radical selected from $(-C(R^{15})_2-)_p$, ($-Z(R^{15})_2-)_p$, or $(-Z(R^{15})_2-C(R^{15})_2-)_p$, Z being silicon, germanium, or tin, $R^{15}$ being $C_{1-6}$ alkyl, p being an integer from 1 to 4; $R^{16}$ is a divalent unsubstituted or alkyl-substituted cyclic alkylene group; and each $R^{17}$ is independently a $C_{1-20}$ linear, branched or cyclic hydrocarbyl group. By using the dinuclear metallocene complex as the catalyst, a high molecular weight olefin polymer can be obtained.

27 Claims, 1 Drawing Sheet

FIG. 1

DINUCLEAR METALLOCENE CATALYST FOR PREPARING HIGH MOLECULAR WEIGHT OLEFIN POLYMER

BACKGROUND OF THE INVENTION

1. Field of the Invention

The present invention relates to a novel dinuclear metallocene complex, and more particularly to a novel metallocene complex that is suitable for preparing olefin polymers having a high molecular weight.

2. Description of the Prior Art

Olefin-based polymers have been used in a wide range of applications. One group of commonly used olefin-based polymers are polyolefins, that is, homopolymers or copolymers of olefins. These polyolefins plastics are typically used in such applications as blow and injection molding, extrusion coating, film and sheeting, pipe, wire and cable.

Most of the physical and mechanical properties of polyolefins, such as their high strength and high impact, stress, and puncture resistances, together with their high toughness, are attributed, at least in part, to their relatively high molecular weight.

An example of polyolefin is ethylene-propylene elastomer (ethylene-propylene rubbers, EPM). It finds many end-use applications due to their resistance to weather, good heat aging properties and their ability to be compounded with large quantities of fillers and plasticizers. Typical automotive uses are radiator and heater hoses, vacuum tubing, weather stripping and sponge doorseals. Typical industrial uses are sponge parts, gaskets and seals.

Another group of commonly used olefin-based polymers are terpolymers of ethylene, propylene, and a non-conjugated diene, which are generally referred to as EPDM elastomers. EPDM elastomers have outstanding weather and acid resistance, and high and low temperature performance properties. Such properties particularly suit EPDM elastomers for use in hoses, gaskets, belts, and bumpers; as blending components for plastics and for tire side walls in the automotive industry; and for roofing applications. Additionally, because of their electrical insulation properties, EPDMs are particularly well suited for use as wire and cable insulation.

In order for EPMs and EPDMs to have commercially acceptable properties, they should have a Mooney viscosity at 127° C. no less than 10, a weight-average molecular weight no less than 110,000, a glass temperature below –40° C., and a degree of crystallinity no greater then 25%.

However, to date, EPMs and EPDMs obtained by catalysis of metallocenes usually have a weight-average molecular weight of 100,000 or less, which does not meet the commercial requirements for an elastomer.

In recent years, it has been found that polyolefins having a multimodal (typically bimodal) molecular weight distribution (MWD) will not only retain the advantageous properties associated with high molecular weight, but also exhibit improved processability.

A bimodal MWD polymer (which can be also simply referred to as "bimodal polymer") is defined as a polymer having two distinct molecular weight distribution curves as observed from gel permeation chromatography (GPC). In other words, a bimodal polymer can be thought of as a mixture containing a first polymer with a relatively higher molecular weight blended together with a second polymer with a relatively lower molecular weight.

Various approaches have been disclosed for producing bimodal polyolefins. The simplest approach is to physically blend together two polymers having different molecular weights. However, this simplistic approach suffers from the problem that homogenization can be obtained only with polymers that can be completely molten. If one of the polymers is not completely molten, then the polymer blend will be inhomogeneous. This can cause a myriad of problems.

U.S. Pat. Nos. 5,284,613 and 5,338,589 disclose a two stage polymerization process for preparing a bimodal polyolefin. In the first stage, olefin monomers are contacted with a catalyst under polymerization conditions to produce a relatively high molecular weight (HMW) polymer, wherein the polymer is deposited on the catalyst particles. In the second stage, the HMW polymer containing the catalyst is further polymerized with additional olefin monomers to produce a relatively low molecular weight (LMW) polymer, much of which is deposited on and within the HMW polymer/catalyst particles from the first stage. The disadvantage of such a two stage process is that two reactors are needed, resulting in an undesirably high capital investment.

U.S. Pat. No. 5,369,194 discloses a process for preparing bimodal polyolefins in a single reactor. The catalyst system so used includes two different transition metal catalysts supported on the same solid support material. Therefore, high and low molecular weight polymers can be formed on the same catalyst particle. The shortcoming is that procedures for preparing the solid support material supporting two different catalysts is complicated and difficult. Moreover, the preferable conditions for activation of the two catalysts may be different. Therefore, when one catalyst is activated, the other catalyst may be inactivated.

SUMMARY OF THE INVENTION

The primary object of the present invention is to solve the above-mentioned problems by providing a novel dinuclear metallocene complex which can be used for preparing a high molecular weight olefin polymer. In addition, since there are two different catalytic sites in a single metallocene complex catalyst, the olefin monomer can be polymerized into a bimodal olefin polymer using a single catalyst in a single reactor, with the catalytic activity of the catalyst comparable to commercially available catalysts.

To achieve the above-mentioned object, a novel dinuclear metallocene complex is developed in the present invention which is represented by the following formula (I):

(I)

wherein
- $M^1$ and $M^2$ are the same or different and are independently selected from the group consisting of Group IIIB, Group IVB and Group VB transition metals,
- each X is the same or different and is indepedently an anionic ligand with −1 valence, which is selected from the group consisting of H, $C_{1-20}$ hydrocarbyl, halogen, $C_{1-20}$ alkoxy, $C_{1-20}$ aryloxy, $NH_2$, $NHR^{11}$, $NR^{11}R^{12}$, —(C=O)$NH_2$, —(C=O)$NHR^{13}$, and —(C=O)$NR^{13}R^{14}$, wherein $R^{11}$, $R^{12}$, $R^{13}$ and $R^{14}$ are $C_{1-20}$ alkyl,
- i is an integer from 1 to 3,
- j is an integer from 1 to 3,
- $R^1$, $R^2$, $R^3$, $R^4$, $R^5$, $R^6$, $R^7$, $R^8$ are the same or different and are independently H, a $C_{1-20}$ linear, branched or cyclic hydrocarbyl group, or a $C_{2-4}$ cyclic hydrocarbylene group which forms a $C_{4-6}$ fused ring system,
- $Y^1$ and $Y^2$ are the same or different and each is an electron-donating group independently selected from a Group 15 or Group 16 element,
- $R^9$ and $R^{10}$ are the same or different and each is a divalent radical selected from (—C($R^{15})_2$—)$_p$, (—Z($R^{15})_2$—)$_p$, or (—Z($R^{15})_2$—C($R^{15})_2$—)$_p$, Z being silicon, germanium, or tin, wherein $R^{15}$ is $C_{1-6}$ alkyl and p is an integer from 1 to 4,
- $R^{16}$ is a divalent unsubstituted or alkyl-substituted cyclic alkylene group, and
- each $R^{17}$ is independently a $C_{1-20}$ linear, branched or cyclic hydrocarbyl group.

DETAILED DESCRIPTION OF THE INVENTION

The present invention relates to a novel dinuclear metallocene complex and a catalyst composition comprising the novel dinuclear metallocene complex and an activating cocatlyst. In particular, the present invention relates to a process for preparing a high molecular weight olefin polymer in the presence of a catalytically effective amount of the novel dinuclear metallocene complex of the present invention.

The novel dinuclear metallocene complex of the present invention is represented by the following formula (I):

(I)

wherein
- $M^1$ and $M^2$ are the same or different and are independently selected from the group consisting of Group IIIB, Group IVB and Group VB transition metals,
- each X is the same or different and is indepedently an anionic ligand with −1 valence, which is selected from the group consisting of H, $C_{1-20}$ hydrocarbyl, halogen, $C_{1-20}$ alkoxy, $C_{1-20}$ aryloxy, $NH_2$, $NHR^{11}$, $NR^{11}R^{12}$, —(C=O)$NH_2$, —(C=O)$NHR^{13}$, and —(C=O)$NR^{13}R^{14}$, wherein $R^{11}$, $R^{12}$, $R^{13}$ and $R^{14}$ are $C_{1-20}$ alkyl,
- i is an integer from 1 to 3,
- j is an integer from 1 to 3,
- $R^1$, $R^2$, $R^3$, $R^4$, $R^5$, $R^6$, $R^7$, $R^8$ are the same or different and are independently H, a $C_{1-20}$ linear, branched or cyclic hydrocarbyl group, or a $C_{2-4}$ cyclic hydrocarbylene group which forms a $C_{4-6}$ fused ring system,
- $Y^1$ and $Y^2$ are the same or different and each is an electron-donating group independently selected from a Group 15 or Group 16 element,
- $R^9$ and $R^{10}$ are the same or different and each is a divalent radical selected from (—C($R^{15})_2$—)$_p$, (—Z($R^{15})_2$—)$_p$, or (—Z($R^{15})_2$—C($R^{15})_2$—)$_p$, Z being silicon, germanium, or tin, wherein $R^{15}$ is $C_{1-6}$ alkyl and p is an integer from 1 to 4,
- $R^{16}$ is a divalent unsubstituted or alkyl-substituted cyclic alkylene group, and
- each $R^{17}$ is independently a $C_{1-20}$ linear, branched or cyclic hydrocarbyl group.

$M^1$ and $M^2$ can be the same or different and each $M^1$ and $M^2$ is independently selected from the group consisting of scandium, yttrium, lanthanum series elements, titanium, zirconium, hafnium, vanadium, niobium, and tantalum. Preferably, $M^1$ and $M^2$ are independently selected from the group consisting of titanium, zirconium, and hafnium.

Each X can be the same or different and is independently an anionic ligand with −1 valence. Preferably, X is selected from the group consisting of H, $C_{1-20}$ hydrocarbyl, halogen, $C_{1-20}$ alkoxy, $C_{1-20}$ aryloxy, —(C=O)NHR$^{13}$, and —(C=O)NR$^{13}$R$^{14}$, wherein $R^{11}$, $R^{12}$, $R^{13}$ and $R^{14}$ are $C_{1-20}$ alkyl.

With regard to the numbers i and j, preferably, the sum of i+2 is equal to the oxidation state of $M^1$ and the sum of j+2 is equal to the oxidation state of $M^2$.

For the substituents on the cyclopentadiene, $R^1$, $R^2$, $R^3$, $R^4$, $R^5$, $R^6$, $R^7$, and $R^8$ are the same or different and are independently H, a $C_{1-20}$ linear, branched or cyclic hydrocarbyl group, or a $C_{2-4}$ cyclic hydrocarbylene group which forms a $C_{4-6}$ fused ring system.

Specifically, the $C_{1-20}$ linear, branched or cyclic hydrocarbyl group can be $C_{1-20}$ alkyl, $C_{1-20}$ alkenyl, $C_{6-20}$ aryl, $C_{7-20}$ alkylaryl, or $C_{7-20}$ arylalkyl. Representative examples include H, methyl, ethyl, propyl, butyl, isobutyl, amyl, isoamyl, hexyl, 2-ethylhexyl, heptyl, octyl, vinyl, allyl, isopropenyl, phenyl, and tolyl.

Specifically, the $C_{2-4}$ cyclic hydrocarbylene group which forms a $C_{4-6}$ fused ring system can be a $C_{2-4}$ cyclic alkylene group. In some cases, at least one of $R^1$, $R^2$, $R^3$, and $R^4$ is a $C_{2-4}$ cyclic alkylene group which forms a $C_{4-6}$ fused ring system. For example, when one of $R^1$, $R^2$, $R^3$, and $R^4$ is a butylene group which forms a fused ring system of six carbon numbers, an indenyl group together with the cyclopentadiene is thus formed. When two of $R^1$, $R^2$, $R^3$, and $R^4$ is a butylene group which forms two fused ring systems of six carbon numbers, a fluorenyl group together with the cyclopentadiene is thus formed.

Similarly, in some cases, at least one of $R^5$, $R^6$, $R^7$, and $R^8$ is a $C_{2-4}$ cyclic alkylene group which forms a $C_{4-6}$ fused ring system. For example, when one of $R^5$, $R^6$, $R^7$, and $R^8$ is a butylene group which forms a fused ring system of six carbon numbers, an indenyl group together with the cyclopentadiene is thus formed. When two of $R^5$, $R^6$, $R^7$, and $R^8$ are butylene groups which form two fused ring systems of six carbon numbers, a fluorenyl group together with the cyclopentadiene is thus formed.

Representative examples of $C_5R^1R^2R^3R^4$ and $C_5R^5R^6R^7R^8$ include $\eta^5$-cyclopentadienyl, $\eta^5$-methylcyclopentadienyl, $\eta^5$-tetramethylcyclopentadienyl, $\eta^5$-pentamethylcyclopentadienyl, $\eta^5$-n-butylcyclopentadienyl, indenyl, tetrahydroindenyl, fluorenyl, and octahydrofluorenyl.

In formula (I), $Y^1$ and $Y^2$ are the same or different and each is an electron-donating group independently selected from a Group 15 or Group 16 element. Representative examples of $Y^1$ and $Y^2$ include nitrogen, phosphorus, arsenic, antimony, oxygen, sulfur, and selenium, preferably nitrogen and phosphorus.

In formula (I), $R^9$ and $R^{10}$ are the same or different and each is a divalent radical selected from (—C(R$^{15}$)$_2$—)$_p$, (—Z(R$^{15}$)$_2$—)$_p$, or (—Z(R$^{15}$)$_2$—C(R$^{15}$)$_2$—)$_p$. Z is silicon, germanium, or tin, preferably silicon, $R^{15}$ is $C_{1-6}$ alkyl, and p is an integer from 1 to 4.

Representative examples of $R^9$ and $R^{10}$ include dimethylmethylene and dimethylsilanylene.

In formula (I), $R^{16}$ is a divalent unsubstituted or alkyl-substituted cyclic alkylene group, preferably, a divalent unsubstituted or $C_{1-10}$ alkyl-substituted $C_{5-12}$ cyclic alkylene group, and most perferably, a divalent unsubstituted or $C_{1-10}$ alkyl-substituted cyclohexylene group. One representative example of such $R^{16}$ is In the present invention, the novel dinuclear metallocene complex can be combined with an activating coatalyst to form a catalyst composition, which can be used for preparing olefin polymers having a high molecular weight.

The activating cocatalyst can be methyl aluminoxane (MAO), a trialkyl aluminum, a dialkyl aluminum halide, a salt of an inert and non-coordinating anion, or a mixture thereof.

The trialkyl aluminum can be selected from the group consisting of trimethyl aluminum, triethyl aluminum, tripropyl aluminum, trisopropyl aluminum, tributyl aluminum, and triisobutyl aluminum (TIBA).

The inert and non-coordinating anion can be a borate. Borates that are suitable for use in the present invention include N,N-dimethyl anilinium tetrakis(pentafluorophenyl) borate, triphenyl carbenium tetrakis(pentafluorophenyl) borate, trimethyl ammonium tetrakis(pentafluorophenyl) borate, ferrocenium tetrakis(pentafluorophenyl)borate, dimethyl ferrocenium tetrakis(pentafluorophenyl)borate, and silver tetrakis(pentafluorophenyl)borate.

Preferably, the activating cocatalyst is methyl aluminoxane, or a mixture of a trialkyl aluminum and a borate.

By using the catalyst composition of the present invention (containing the novel dinuclear metallocene complex and the activating cocatalyst), an olefin polymer can be synthesized. In the presence of a catalytically effective amount of the metallocene complex catalyst of the present invention under polymerizing conditions, at least one olefin monomer can be subjected to polymerization, or at least one olefin monomer together with another monomer can be subjected to polymerization.

Suitable olefin monomers can be ethylene or α-olefins. The polymers to be prepared by the process of the present invention can be homopolymers of ethylene, homopolymers of α-olefins, copolymers of α-olefins, and copolymers of ethylene and αolefins. Examples of the α-olefins include those olefins having 3 to 12 carbon atoms, such as propylene, 1-butene, 1-pentene, 1-hexene, and 1-octene.

More particularly, the catalyst system disclosed in the present invention can be advantageously used to prepare ethylene homopolymers, including high density polyethylene (HDPE) having broad, bimodal, or multimodal, molecular weight distributions for applications such as high molecular weight films and blow molding.

Furthermore, the catalyst system disclosed in the present invention can be advantageously used to prepare a copolymer of ethylene and propylene (EPM). Also, a copolymer of ethylene, a $C_{3-12}$ α-olefin, and a non-conjugated diene can be prepared. More particularly, when the $C_{3-12}$ α-olefin used is propylene, a copolymer of ethylene, propylene, and a non-conjugated diene can be prepared, which is referred to as EPDM. The suitable non-conjugated diene can be 5-ethylidene-2-norbornene (ENB), 5-methylene-2-norbornene, 5-vinylidene-2-norbornene, 1,4-hexadiene (HD), or dicyclopentadiene (DCPD).

The polymerization can also be carried out in the presence of hydrogen together with the catalyst composition. Thus, the molecular weight of the resulting polymer can be controlled to any desired range.

The novel catalyst system disclosed in the present invention can be used in slurry reaction conditions, gas phase, and solution polymerization reaction conditions. Polymerization is typically carried out at a temperature of 0° to 250° C., and an atmospheric pressure up to 3,000 psi.

The most important advantage of the present invention is that by using the novel dinuclear metallocene as a catalyst, a olefin polymer having a high molecular weight greater than 200,000 can be obtained. While using a conventional metallocene, the molecular weight of the obtained olefin polymer can only reach about 100,000.

In addition, since the metallocene of the present invention is dinuclear, that is, has two metal centers, and the chemical enviroments around these two metal centers are different, thus, there are two different catalytic sites in a single metallocene. Therefore, a bimodal olefin polymer can be obtained by using such dinuclear metallocene as a catalyst.

The following examples are intended to illustrate the process and the advantages of the present invention more fully without limiting its scope, since numerous modifications and variations will be apparent to those skilled in the art.

Synthesis of Metallocene

EXAMPLE 1

1,8-diamino-p-menthane (7.37 g, 30.3 mmole, 70–75% purity) was loaded in a 300 mL round bottom flask with 150 mL of ether. This yellow solution was cooled to −78° C. before 2 equivalents of 1.6 M n-butyl lithium (n-BuLi) was injected into it with a syringe. The mixture was slowly warmed up to room temperature and stirred overnight. It was filtered to collect 6.8 g of a dilithium salt as a white solid.

EXAMPLE 2

The dilithium salt (1.97 g, 10.8 mmole) obtained from Example 1 and tetramethylcyclopentadienyl-dimethylsilyl chloride (4.65 g, 21.67 mmole) were dissolved in 50 mL and 20 mL of THF separately. These two solutions were combined at room temperature and the mixture was allowed to stir overnight. This yellow mixture was stripped to a thick oil and was extracted with 40 mL of toluene. It was filtered to remove the LiCl solid and the filtrate was stripped again to a yellow oil (5.6 g, 10.63 mmole).

EXAMPLE 3

The ligand (5.6 g, 10.63 mmole) obtained from Example 2 was dissolved in 100 mL of THF to give a yellow solution. This solution was cooled to −78° C. before 4 equivalents of 1.6 M n-BuLi (42.5 mmole) was injected into it with a syringe. The light brown solution mixture was slowly warmed up to room temperature and became orange in color. After being stirred overnight, the mixture was stripped to about 10 mL and 20 mL of toluene and 20 mL of pentane were added to it sequentially. The mixture was filtered and 5.1 g of a tetralithium salt as a white solid was collected.

EXAMPLE 4

The tetralithium salt (3.0 g, 5.45 mmole) obtained from Example 3 was completely dissolved in 30 mL of THF. Two equivalents of $TiCl_3(thf)_3$ (4.03 g, 10.9 mmole) was suspended in THF. These two solutions were cooled to −30° C. before being combined. This mixture was stirred for 3 hours before 2.5 g of AgCl (excess) was added to it. The reaction mixture turned black rather quickly and turned reddish while stirring overnight. The mixture was stripped to dryness and extracted with 35 mL of toluene. It was filtered to remove any insolubles and the reddish brown filtrate was concentrated to low volume. The concentrated filtrate was subjected to fractional crystallization to afford 0.5 g of the final product as light brown solid.

Polymer Synthesis

Synthesis of EPM (Ethylene Propylene Rubber)

EXAMPLE 5

After the reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 80° C., and 500 mL of toluene was charged into the reactor. After the temperature was stable, 8 mL of MAO($1.2 \times 10^{-2}$ mole of methyl aluminoxane (MAO) in toluene) was charged into the reactor and stirred. After 5 minutes, 2 mL ($4 \times 10^{-6}$ mole) of the catalyst obtained from Example 4 in toluene was charged and stirred. After stirring at 80° C. for 1 minutes, ethylene and propylene gas (ratio in volume: 40/50) at 100 psi was introduced into the reactor.

After the completion of the polymerization reaction, the solution was cooled and methanol was added to precipitate the product. The product was filtered and dried for various tests. The results are shown in Table 1.

EXAMPLES 6–11

The same procedures as described in Example 5 were employed, except that the reaction temperature, the reactants ratio (ethylene/propylene, E/P), or the reaction pressure was changed. The results are shown in Table 1.

Figure 1:
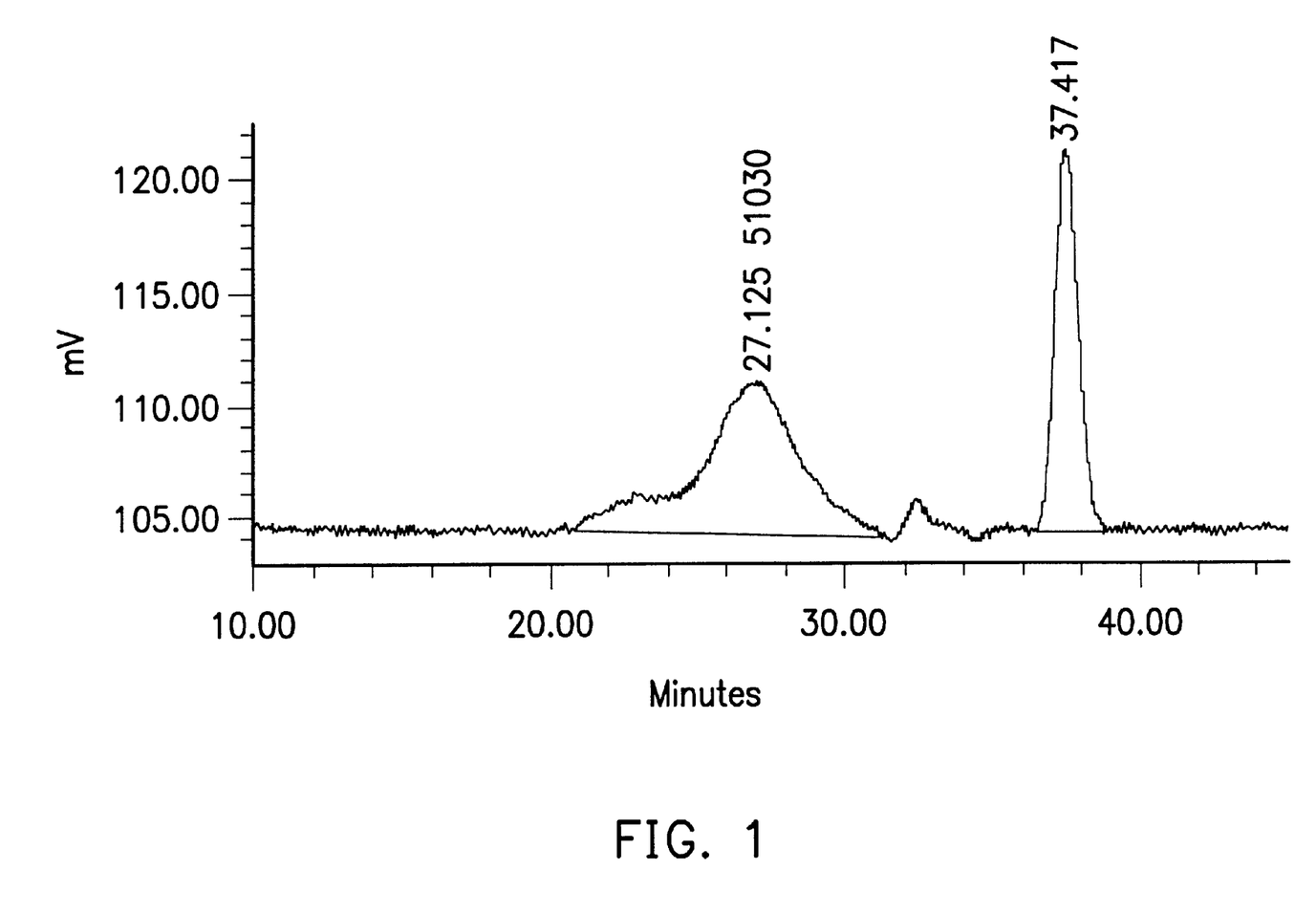
FIG. 1 shows the GPC diagram of the product obtained from Example 9, indicating that the resulting polymer is a bimodal ethylene/propylene polymer.

FIG. 1 shows the GPC diagram of the product obtained from Example 9, indicating that the resulting polymer is a bimodal ethylene/propylene polymer.

TABLE 1

| | Reaction Conditions | | | | Properties of the Products | | | |
|---|---|---|---|---|---|---|---|---|
| Example | Temp (° C.) | E/P volume ratio | Pressure (psi) | Activity (× $10^4$ g/g-metal-hr) | Tg (° C.) | E/P mole ratio | Mw | MWD |
| 5 | 80 | 40/50 | 100 | 4.22 | −47.8 | 68/32 | 394,468 | 4.6 |
| 6 | 100 | 40/50 | 100 | 4.07 | −48.2 | 68/32 | 292,923 | 2.7 |
| 7 | 120 | 40/50 | 100 | 3.64 | −47.5 | 70/30 | 249,935 | 5.9 |
| 8 | 80 | 50/50 | 100 | 3.12 | −47.3 | 68/32 | 519,131 | 3.7 |
| 9 | 80 | 40/60 | 100 | 2.37 | −48.3 | 68/32 | 190,826 | 6.00 |
| 10 | 100 | 40/50 | 80 | 3.62 | −45 | 70/30 | 539,527 | 3.3 |
| 11 | 100 | 40/50 | 120 | 4.12 | −45.1 | 75/25 | 387,194 | 3.3 |

Synthesis of EPDM (Ethylene Propylene Diene Rubber)

EXAMPLE 12

The reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 80° C., and 500 mL of toluene was charged into the reactor. After the temperature was stable, 8 mL ($1.2 \times 10^{-2}$ mole) of MAO was charged into the reactor and stirred. After 5 minutes, 2 mL ($4 \times 10^{-6}$ mole) of the catalyst obtained from Example 4 in toluene was charged and stirred. After stirring at 80° C. for 5 minutes, 10 mL of 5-ethylidene-2-norbornene (ENB) was charged and stirred. After 1 minute, ethylene and propylene gas (ratio in volume: 40/50) at 100 psi was introduced into the reactor.

After the completion of the polymerization reaction, the solution was cooled and methanol was added to precipitate the product. The product was filtered and dried for various tests. The results are shown in Table 2.

EXAMPLE 13

The same procedures as described in Example 12 were employed, except that ethylene/propylene (E/P) feed ratio was changed. The results are shown in Table 2.

EXAMPLE 14

The reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 80° C., and 500 mL of toluene was charged into the reactor. After the temperature was stable, 8 mL ($1.2 \times 10^{-2}$ mole) of MAO was charged into the reactor and stirred. After 5 minutes, 2 mL ($4 \times 10^{-6}$ mole) of the catalyst obtained from Example 4 in toluene was charged and stirred. After stirring at 80° C. for 1 minutes, a mixture gas of hydrogen and nitrogen (7% $H_2$) at 7 psi was introduced into the reactor. After stirring 1 minute, ethylene and propylene gas (ratio in volume: 40/50) at 100 psi was introduced into the reactor.

After the completion of the polymerization reaction, the solution was cooled. Methanol was added to precipitate the product. The product was filtered and dried for various tests. The results are shown in Table 3.

EXAMPLES 15–17

The same procedures as described in Example 14 were employed, except that the pressure of the $H_2/N_2$ gas was changed. The results are shown in Table 3.

EXAMPLE 18

The reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 80° C., and 500 mL of toluene was charged into the reactor. After the temperature was stable, 8 mL ($1.2 \times 10^{-2}$ mole of methyl aluminoxane (MAO) in toluene was charged into the reactor and stirred. After 5 minutes, 2 mL ($4 \times 10^{-6}$ mole) of the catalyst obtained from Example 4 in toluene was charged and stirred. After stirring at 80° C. for 5 minutes, 10 mL of ENB was added and stirred. After stirring for 1 minute, a gas mixture of hydrogen and nitrogen (7% $H_2$) at 7 psi was introduced into the reactor. After stirring 1 minute, ethylene and propylene gas (ratio in volume: 40/50) at 100 psi was introduced into the reactor.

After the completion of the polymerization reaction, the solution was cooled and methanol was added to precipitate the product. The product was filtered and dried for various tests. The results are shown in Table 3.

Mw Control by $H_2$ Introduction

TABLE 2

| | Reaction Conditions | | | | | Properties of the Products | | | |
|---|---|---|---|---|---|---|---|---|---|
| Example | Temp (° C.) | E/P volume ratio | ENB (mL) | Pressure (psi) | Activity (× $10^4$ g/g-metal-hr) | Tg (° C.) | E/P mole ratio | ENB content (mole %) | Mw | MWD |
| 5 | 80 | 40/50 | 0 | 100 | 4.22 | −47.8 | 68/32 | 0 | 394,468 | 4.6 |
| 12 | 80 | 40/50 | 10 | 100 | 3.06 | −31.4 | 79/21 | 1 | 325,050 | 4.32 |
| 13 | 80 | 50/50 | 10 | 100 | 2.4 | −49.1 | 79/21 | 1.7 | 499,008 | 2.71 |
| 14 | 80 | 40/50 | 0 | 100 | 3.9 | −46.8 | 60/40 | 0 | 339,038 | 4.2 |

TABLE 3

| Example | Reaction Conditions | | | Properties of the Products | | | |
|---|---|---|---|---|---|---|---|
| | ENB (mL) | hydrogen (7%) pressure (psi) | Activity (× 10⁴ g/g-metal-hr) | Tg (° C.) | E/P mole ratio | Mw | MWD |
| 14 | 0 | 7 | 3.9 | −46.8 | 60/40 | 339,038 | 4.2 |
| 15 | 0 | 14 | 3.8 | −46.5 | 53/47 | 237,453 | 3.1 |
| 16 | 0 | 28 | 3.5 | −47.2 | 58/42 | 261,720 | 3.6 |
| 17 | 0 | 42 | 3.2 | | 57/43 | 155,291 | 3.2 |
| 18 | 10 | 14 | 3.8 | −42.2 | 56/44 | 308,596 | 2.4 |

Reaction Temp = 80° C.
E/P Feed Ratio = 40/50
Pressure = 100 psi

Ethylene Homopolymerization

EXAMPLE 19

The 450 mL reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 100° C. After the temperature was stable, 250 mL of toluene and $1.49 \times 10^{-2}$ mole of 10% MAO solution were charged into the reactor and stirred. After stirring for 5 minutes, $2 \times 10^{-6}$ mole of the catalyst obtained from Example 4 was charged and stirred for 3 minutes. Ethylene gas at 150 psi was introduced into the reactor and the reaction proceeded for 30 minutes.

After the completion of the polymerization reaction, the solution was cooled and 10 mL of isopropanol (IPA) was added to deactivate the activity of the catalyst and cocatalyst. Methanol was added to precipitate the product. After filtration and drying at 80° C. for 10 hours, the polyethylene product was obtained. The results are shown in Table 4.

EXAMPLES 20–21

The same procedures as described in Example 19 were employed, except that the reaction temperature was changed. The results are shown in Table 4.

TABLE 4

| Example | Reaction Temperature (° C.) | Activity (× 10⁴ g/g-metal-hr) | Properties of the Products | | |
|---|---|---|---|---|---|
| | | | Tm (° C.) | Mw | MWD |
| 19 | 80 | 3.6 | 132 | 1,340,673 | 3.1 |
| 20 | 100 | 4.59 | 131 | 521,772 | 5.4 |
| 21 | 120 | 3.83 | 132 | 445,464 | 2.33 |

Ethylene Copolymerization

EXAMPLE 22

The reactor vessel was heated to 105° C., nitrogen gas was introduced for 5 minutes to purge oxygen from the reactor. The reactor was then evacuated for about 2 hours to ensure complete removal of moisture and oxygen. The reactor temperature was adjusted to 100° C. After the temperature was stable, 250 mL of toluene, 5 mL of octene-1, and $1.49 \times 10^{-2}$ mole of 10% MAO solution were charged into the reactor and stirred. After stirring for 5 minutes, $2 \times 10^{-6}$ mole of the catalyst obtained from Example 4 was charged and stirred for 3 minutes. Ethylene gas at 150 psi was introduced into the reactor and the reaction proceeded for 30 minutes.

After the completion of the polymerization reaction, the solution was cooled and 10 mL of isopropanol (IPA) was added to deactivate the activity of the catalyst and cocatalyst. Methanol was added to precipitate the product. After filtration and drying at 80° C. for 10 hours, the ethylene/octene-1 copolymer was obtained. The results are shown in Table 5.

EXAMPLES 23–25

The same procedures as described in Example 22 were employed, except that the species or amount of the comonomer was changed. The results are shown in Table 5.

TABLE 5

| Example | Reaction Temperature (° C.) | Comonomer | Activity (× 10⁴ g/g-metal-hr) | Properties of the Products | | |
|---|---|---|---|---|---|---|
| | | | | Tm (° C.) | Mw | MWD |
| 20 | 100 | — | 4.59 | 131 | 521,772 | 5.4 |
| 22 | 100 | 1-$C_8$, 20 mL | 11.2 | — | 196,904 | 2.75 |
| 23 | 100 | 1-$C_8$, 10 mL | 9.44 | — | 212,650 | 2.6 |
| 24 | 100 | 1-$C_8$, 5 mL | 5.61 | 102 | 397,891 | 2.77 |
| 25 | 100 | 1-$C_6$, 5 mL | 4.85 | 97 | 355,795 | 3.86 |

EXAMPLE 26

Four kinds of commercial EPDMs, Uniroyal 509, Exxon 8731, DuPont Dow 4520, DuPont Dow 5750P, and the EPM obtained from Example 8 of the present invention are subjected to various forms of analysis to compare their processing properties. Uniroyal 509 and Exxon 8731 are EPDMs obtained by a non-metallocene vanadium type catalyst. DuPont Dow 4520 and DuPont Dow 5750P are EPDMs obtained by a constrained geometry catalyst (CGC), which is mononuclear. TC90 (min) with DCP at 170° C. indicates the time required for 90% of polymer to become crosslinked by catalysis of dicumyl peroxide (DCP) at 170° C. A smaller TC90 indicates faster curing rate.

The analysis results are shown in Table 6. It can be seen that the EPM obtained by the novel catalyst of the present invention has a higher Mooney viscosity at 125° C., attributed mainly to its higher molecular weight than the EPDMs obtained by conventional catalysts. In fact, the Mw of the EPM obtained from Example 8 is 519,131 (see Table 1). Moreover, the EPM obtained by the novel catalyst of the present invention has a faster cross-linking rate, indicating that it has better processibility than the EPDMs obtained by conventional catalysts.

TABLE 6

| Samples | ethylene content (%) | ENB content (%) | Mooney at 125° C. | Tg (° C.) | TC90 (min) DCP at 170° C. |
|---|---|---|---|---|---|
| Uniroyal 509 | 70 | 9 | 56 | −46.2 | 7.94 |
| Exxon 8731 | 75 | 3 | 26 | −41.3 | 8.63 |
| DuPont-Dow 4520 | 51 | 5 | 20 | −53.6 | 9.52 |
| DuPont-Dow 5750P | 69 | 9 | 50 | −36.6 | 9.66 |
| EPM obtained from Example 8 of the present invention | 68 | — | 100 | −47.3 | 5.1 |

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A dinuclear metallocene complex which is represented by the following formula (I):

(I)

wherein $M^1$ and $M^2$ are the same or different and are independently selected from the group consisting of Group 3, Group 4, and Group 5 transition metals, each X is the same or different and is independently an anionic ligand with −1 valence, which is selected from the group consisting of H, $C_{1-20}$ hydrocarbyl, halogen, $C_{1-20}$ alkoxy, $C_{1-20}$ aryloxy, $NH_2$, $NHR^{11}$, $NR^{11}R^{12}$, —(C=O)$NH_2$, —(C=O)$NHR^{13}$, and —(C=O)$NR^{13}R^{14}$, wherein $R^{11}$, $R^{12}$, $R^{13}$ and $R^{14}$ are $C_{1-20}$ alkyl, i is an integer from 1 to 3, j is an integer from 1 to 3, $R^1$, $R^2$, $R^3$, $R^4$, $R^5$, $R^6$, $R^7$, $R^8$ are the same or different and are independently H, a $C_{1-20}$ linear, branched or cyclic hydrocarbyl group, or a $C_{2-4}$ cyclic hydrocarbylene group which forms a $C_{4-6}$ fused ring system, $Y^1$ and $Y^2$ are the same or different and each is an electron-donating group independently selected from a Group 15 or Group 16 element, $R^9$ and $R^{10}$ are the same or different and each is a divalent radical selected from $(-C(R^{15})_2-)_p$, $(-Z(R^{15})_2-)_p$, or $(-Z(R^{15})_2-C(R^{15})_2-)_p$, Z being silicon, germanium, or tin, wherein $R^{15}$ is $C_{1-6}$ alkyl and p is an integer from 1 to 4, $R^{16}$ is a divalent unsubstituted or alkyl-substituted cyclic alkylene group, and each $R^{17}$ is independently a $C_{1-20}$ linear, branched or cyclic hydrocarbyl group.

2. The metallocene complex as claimed in claim 1, wherein $M^1$ and $M^2$ are independently selected from the group consisting of scandium, yttrium, lanthanum series elements, titanium, zirconium, hafnium, vanadium, niobium, and tantalum.

3. The metallocene complex as claimed in claim 1, wherein $M^1$ and $M^2$ are independently selected from the group consisting of titanium, zirconium, and hafnium.

4. The metallocene complex as claimed in claim 1, wherein $M^1$ and $M^2$ are the same.

5. The metallocene complex as claimed in claim 4, wherein $M^1$ and $M^2$ are titanium.

6. The metallocene complex as claimed in claim 1, wherein X is selected from the group consisting of H, $C_{1-20}$ hydrocarbyl, halogen, $C_{1-20}$ alkoxy, $C_{1-20}$ aryloxy, —(C=O)NHR$^{13}$, and —(C=O)NR$^{13}$R$^{14}$, wherein of $R^{11}$, $R^{12}$, $R^{13}$ and $R^{14}$ are $C_{1-20}$ alkyl.

7. The metallocene complex as claimed in claim 1, wherein X is halogen.

8. The metallocene complex as claimed in claim 1, wherein the sum of i+2 is equal to the oxidation state of $M^1$.

9. The metallocene complex as claimed in claim 8, wherein i is 2 and $M^1$ is titanium.

10. The metallocene complex as claimed in claim 1, wherein the sum of j+2 is equal to the oxidation state of $M^2$.

11. The metallocene complex as claimed in claim 10, wherein j is 2 and $M^2$ is titanium.

12. The metallocene complex as claimed in claim 1, wherein $R^1$, $R^2$, $R^3$, $R^4$, $R^5$, $R^6$, $R^7$, and $R^8$ are the same or different and are independently selected from H or a $C_{1-20}$ hydrocarbyl group, the $C_{1-20}$ hydrocarbyl group being $C_{1-20}$ alkyl, $C_{1-20}$ alkenyl, $C_{6-20}$ aryl, $C_{7-20}$ alkylaryl, or $C_{7-20}$ arylalkyl.

13. The metallocene complex as claimed in claim 12, wherein $R^1$, $R^2$, $R^3$, $R^4$, $R^5$, $R^6$, $R^7$, and $R^8$ are the same or different and are independently selected from H, methyl, ethyl, propyl, butyl, isobutyl, amyl, isoamyl, hexyl, 2-ethylhexyl, heptyl, octyl, vinyl, allyl, isopropenyl, phenyl, or tolyl.

14. The metallocene complex as claimed in claim 1, wherein at least one of $R^1$, $R^2$, $R^3$, and $R^4$ is a $C_{2-4}$ cyclic alkylene group which forms a $C_{4-6}$ fused ring system.

15. The metallocene complex as claimed in claim 1, wherein at least one of $R^5$, $R^6$, $R^7$, and $R^8$ is a $C_{2-4}$ cyclic alkylene group which forms a $C_{4-6}$ fused ring system.

16. The metallocene complex as claimed in claim 14, wherein one of $R^1$, $R^2$, $R^3$, and $R^4$ is a butylene group which forms a fused ring system of six carbon numbers and forms an indenyl group together with the cyclopentadiene.

17. The metallocene complex as claimed in claim 14, wherein two of $R^1$, $R^2$, $R^3$, and $R^4$ are a butylene groups which form two fused ring systems of six carbon numbers and form a fluorenyl group together with the cyclopentadiene.

18. The metallocene complex as claimed in claim 15, wherein one of $R^5$, $R^6$, $R^7$, and $R^8$ is a butylene group which forms a fused ring system of six carbon numbers and forms an indenyl group together with the cyclopentadiene.

19. The metallocene complex as claimed in claim 15, wherein two of $R^5$, $R^6$, $R^7$, and $R^8$ are butylene groups which form two fused ring systems of six carbon numbers and form a fluorenyl group together with the cyclopentadiene.

20. The metallocene complex as claimed in claim 1, wherein $C_5R^1R^2R^3R^4$ and $C_5R^5R^6R^7R^8$ are selected from the group consisting of $\eta^5$-cyclopentadienyl, $\eta^5$-methylcyclopentadienyl, $\eta^5$-tetramethylcyclopentadienyl, $\eta^5$-pentamethylcyclopentadienyl, $\eta^5$-n-butylcyclopentadienyl, indenyl, tetrahydroindenyl, fluorenyl, and octahydrofluorenyl.

21. The metallocene complex as claimed in claim 1, wherein $Y^1$ and $Y^2$ are independently selected from the group consisting of nitrogen, phosphorus, arsenic, antimony, oxygen, sulfur, and selenium.

22. The metallocene complex as claimed in claim 21, wherein $Y^1$ and $Y^2$ are independently selected from nitrogen and phosphorus.

23. The metallocene complex as claimed in claim 1, wherein Z is silicon.

24. The metallocene complex as claimed in claim 1, wherein $R^9$ and $R^{10}$ are divalent radicals selected from dimethylmethylene and dimethylsilanylene.

25. The metallocene complex as claimed in claim 1, wherein $R^{16}$ is a divalent unsubstituted or $C_{1-10}$ alkyl-substituted $C_{5-12}$ cyclic alkylene group.

26. The metallocene complex as claimed in claim 25, wherein $R^{16}$ is a divalent unsubstituted or $C_{1-10}$ alkyl-substituted cyclohexylene group.

27. The metallocene complex as claimed in claim 26, wherein $R^{16}$ is

* * * * *